United States Patent
Kent et al.

(10) Patent No.: US 7,256,362 B2
(45) Date of Patent: *Aug. 14, 2007

(54) MECHANICAL LIMITER SWITCH

(75) Inventors: Harold B. Kent, Portola Valley, CA (US); James J. Levante, Redwood City, CA (US); Aaron T. Fine, Alviso, CA (US); Joseph R. Layton, Sunnyvale, CA (US)

(73) Assignee: Medconx, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/038,575

(22) Filed: Jan. 21, 2005

(65) Prior Publication Data

US 2005/0252756 A1    Nov. 17, 2005

Related U.S. Application Data (63) Continuation of application No. 10/739,252, filed on Dec. 17, 2003, now Pat. No. 6,846,996.

(60) Provisional application No. 60/434,297, filed on Dec. 17, 2002.

(51) Int. Cl.
  *H01H 1/12* (2006.01)
  *H01H 1/34* (2006.01)
  *H01H 3/12* (2006.01)
  *H01H 13/50* (2006.01)

(52) U.S. Cl. ............... 200/276.1; 200/290; 200/520; 200/535

(58) Field of Classification Search ... 200/51 R–51.17, 200/275, 276, 276.1, 290, 520–536, 17 R, 200/61.08, 300, 341, 47

See application file for complete search history.

(56) References Cited

U.S. PATENT DOCUMENTS 3,226,496 A    12/1965    Seabury, Jr. ................ 200/8 R (Continued)

FOREIGN PATENT DOCUMENTS

| DE | 2106716 A1 | 8/1972 |
| GB | 617 114 A | 2/1949 |
| WO | WO 01/80932 | 11/2001 |

OTHER PUBLICATIONS

Supplementary European Search Report from EP 03 80 0105, mailed Jul. 13, 2006.

*Primary Examiner*—Michael A. Friedhofer
(74) *Attorney, Agent, or Firm*—Jones Day (57) ABSTRACT

A mechanical limiter switch for use in a medical or surgical device has a substantially cylindrically shaped housing with a perimeter and an opening in an axial direction. The housing has a pattern along the perimeter. A spring is mounted in the opening along the axial direction, and is pre-stressed for movement in a radial direction and pre-stressed for movement in the axial direction. The spring has a radial member protruding through the pattern of the housing. A plunger is mounted in the opening along the axial direction, abutting the spring for urging the spring in the axial direction and for moving the member in the pattern along the perimeter. After a pre-determined number of activations of the plunger in the axial direction, the member will come to a terminating position and will either contact a pin to establish electrical continuity or at the terminating position break electrical continuity.

20 Claims, 8 Drawing Sheets

U.S. PATENT DOCUMENTS

| | | | |
|---|---|---|---|
| 3,548,137 A | 12/1970 | Farrell et al. | 200/276 |
| 4,012,613 A * | 3/1977 | Watson | 200/61.08 |
| 4,238,653 A * | 12/1980 | Brandt | 200/524 |
| 4,284,862 A | 8/1981 | Overman et al. | 200/276 |
| 4,313,685 A | 2/1982 | Stahl et al. | 200/520 |
| 4,533,803 A | 8/1985 | Beller et al. | 200/290 |
| 5,584,384 A * | 12/1996 | Mizuno et al. | 200/524 |
| 5,841,085 A * | 11/1998 | Rittinghaus et al. | 200/16 R |
| 6,198,056 B1 * | 3/2001 | Wisinski | 200/17 R |
| 6,204,463 B1 | 3/2001 | Stringos | 200/520 |
| 6,846,996 B2 * | 1/2005 | Kent et al. | 200/276.1 |
| 2001/0018918 A1 | 9/2001 | Burnside et al. | 128/897 |
| 2003/0233087 A1 | 12/2003 | Chen et al. | 606/41 |
| 2004/0245079 A1 | 12/2004 | Kent et al. | 200/276.1 |

* cited by examiner

MECHANICAL LIMITER SWITCH

This application claims the priority of a co-pending provisional application 60/434,297 filed on Dec. 17, 2002.

TECHNICAL FIELD

The present invention relates to a mechanical limiter switch and more particularly to a limiter switch for use in a medical or surgical device wherein said switch limits the operation of the device after a pre-determined number of operations.

BACKGROUND OF THE INVENTION

Current methods to limit the number of uses of electrical devices, such as those used in surgical procedures or other health or medical related applications have relied upon regulatory actions, such as regulations promulgated by the United Stated FDA and the European Regulatory body (EUR). Clearly, this method relies upon the user to adhere to those regulations subject to penalties for non-compliance. Thus, this is only a self-adhering method to limit the use of these devices.

Minimally invasive surgical devices comprise most of the electrical devices whose use is limited by regulatory action. These devices can be expensive and reimbursement for their use can be tightly controlled by health insurance. Further, in many parts of the lesser-developed countries of the world, availability can be limited. These devices are regulated to limit the amount of usage because of efficacy, sterility, and to limit cross contamination etc. Within the US, tracking of the devices by lot and serial number is required in the entire distribution channel to the end use. The tracking system, along with the threat of lawsuit, creates a barrier to misuse. However, outside of the US where the tort system is not as well developed, multiple misuses can occur with greater frequency. These factors present a potential liability for the manufacturer of these devices along with the associated tarnishing of goodwill and reputation to the manufacturer.

Another prior art method has been the implementation of electrical circuits with associated electronic integrated circuits, and associated software to limit the use of the device. This "solution" has at least two limitations. First, they cannot be used to retrofit existing devices easily. Since such devices must work with an electronic controller that manages the device, the retrofitting of the existing devices may necessitate a retrofit of the controller. Second, one of the most effective method of sterilizing these devices is through the use of gamma radiation (or x-ray). X rays potentially can destroy integrated circuits and/or alter the content of memory and integrated circuits, thereby altering the software in an uncontrollable manner.

Hence, there is a need for a limiter switch that can be used in a surgical or medical device to limit the amount of uses of such devices that is both easy to use and is immune to most sterilization techniques, and is stable in all known forms of sterilization, e.g. Gamma, ETO, E-Beam, Auto-Clave, etc.

SUMMARY OF THE INVENTION

Accordingly, in the present invention, a limiter switch is comprised of a substantially cylindrically shaped housing having a perimeter and an opening in an axial direction. The housing has a pattern on the perimeter. A spring is mounted in the opening along the axial direction. The spring has a radial member protruding through the pattern. A plunger is mounted in the opening along the axial direction, abutting the spring for urging the spring in the axial direction and for moving the member rotationally in the pattern along the perimeter. After a pre-determined number of activations of the plunger in the axial direction, the member will either contact a contact pin to establish an electrical continuity or come to a terminating position that breaks electrical continuity.

BRIEF DESCRIPTION OF THE DRAWINGS

FIG. 6b is a side-enlarged view of the pattern shown in FIG. 6a.

FIG. 9b is a fully assembled perspective view of the embodiment of the switch shown in FIG. 9a.

FIG. 10b is a fully assembled perspective view of the embodiment of the switch shown in FIG. 10a.

FIG. 11b is a fully assembled perspective view of the embodiment of the switch shown in FIG. 11a.

DETAILED DESCRIPTION OF THE PREFERRED EMBODIMENTS

Figure 1:
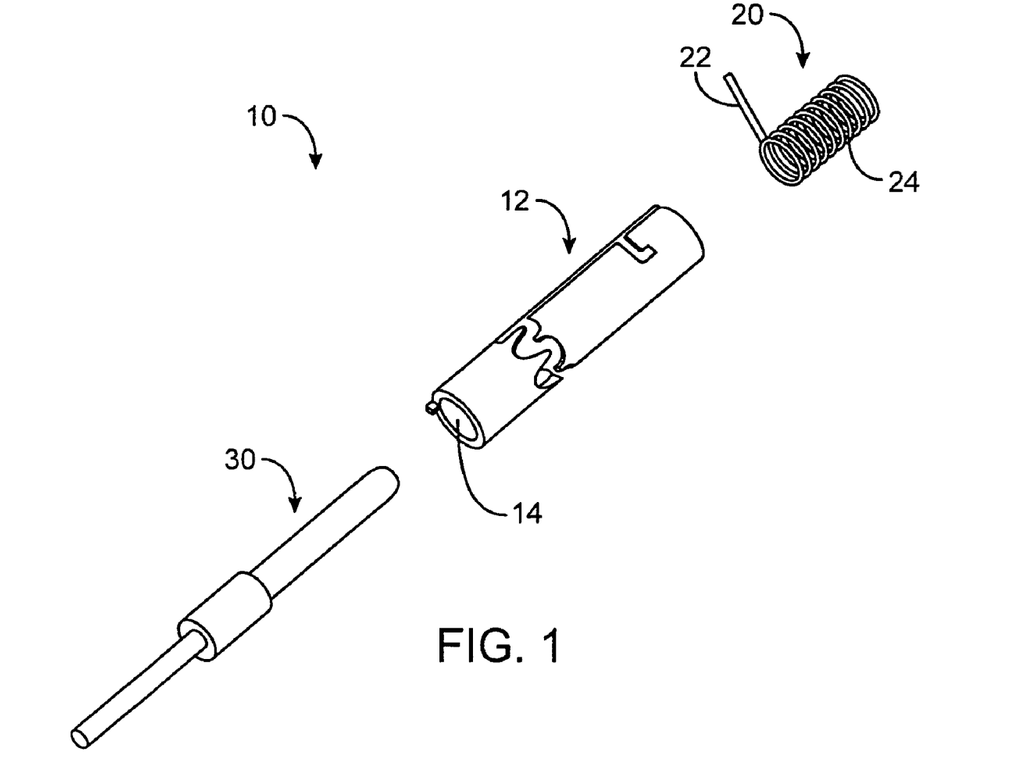
FIG. 1 is an exploded view of one embodiment of a mechanical limiter switch of the present invention.

Referring to FIG. 1, there is shown an exploded view of a mechanical limiter switch 10 of the present invention. The switch 10 comprises a housing 12, which is substantially cylindrically shaped and has an outer perimeter, and an opening 14 in an axial direction. The housing 12 has a pattern 16 along its perimeter. In a preferred embodiment, the pattern 16 is zigzag shaped; having crests 16a and troughs 16b (shown in FIG. 6b). The housing 12 also has a notch 18 (shown in FIG. 2). A spring 20 is positioned axially in the opening 14 of the housing 12. The spring 20 has a member 22 near a first end, which extends radially from the spring 20. The spring 20 has a second end 24. The spring 20 is mounted in the axial opening 14 of the housing 12 such that the second end 24 is anchored in the notch 18, and the member 22 protruding through the pattern opening 16 of the housing 12. When the spring 20 is so positioned, it is pre-tensioned in the radial direction. Thus, as the spring 20 is placed in the axial opening 14, the member 22 is positioned to protrude through the pattern opening 16. The spring 20 is then radially twisted and axially compressed to pre-tension the spring 20, and the second end 24 is then anchored at the notch 18. In one embodiment, the second end 24 also comprises a radial protrusion. Thus, the spring 20 is anchored by placing the second end 24 through the notch 18. Finally, the switch 10 comprises a plunger 30. The plunger 30 moves in an axial direction in the axial opening 14 of the housing 12 and urges or acts against the spring 20.

Figure 2:
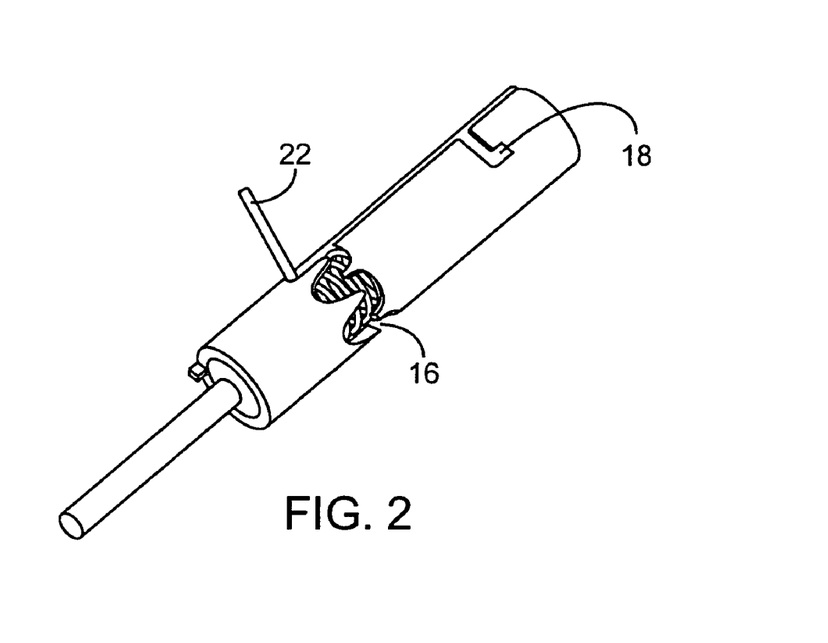
FIG. 2 is perspective view of a fully assembled mechanical limiter switch of the embodiment shown in FIG. 1.
Figure 3A:
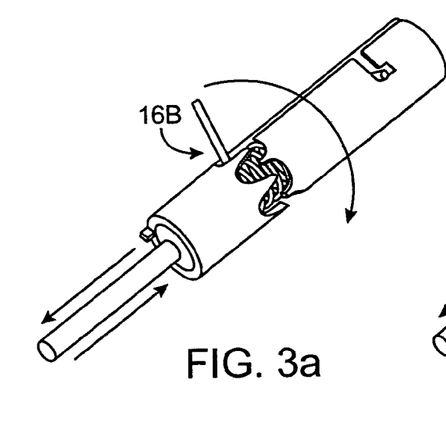
FIGS. 3a-3f are perspective views showing the operation of the switch shown in FIG. 2.
Figure 3B:
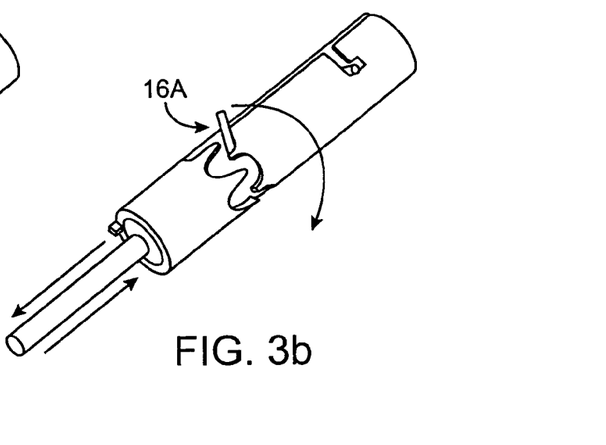
Figure 3C:
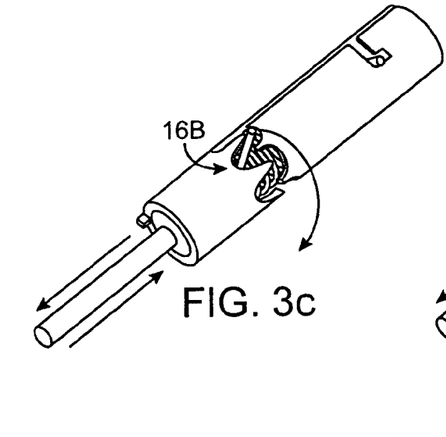
Figure 3D:
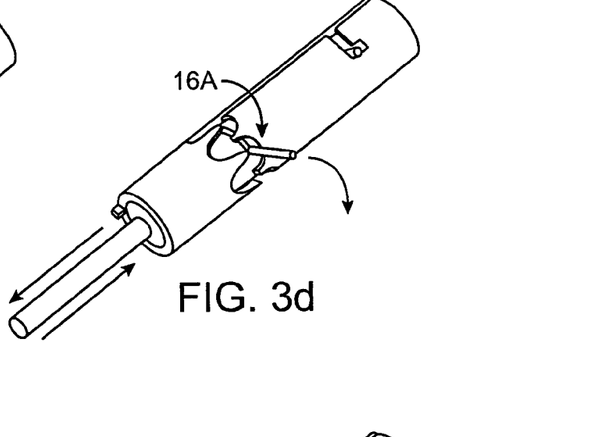
Figures 3E, 3F:
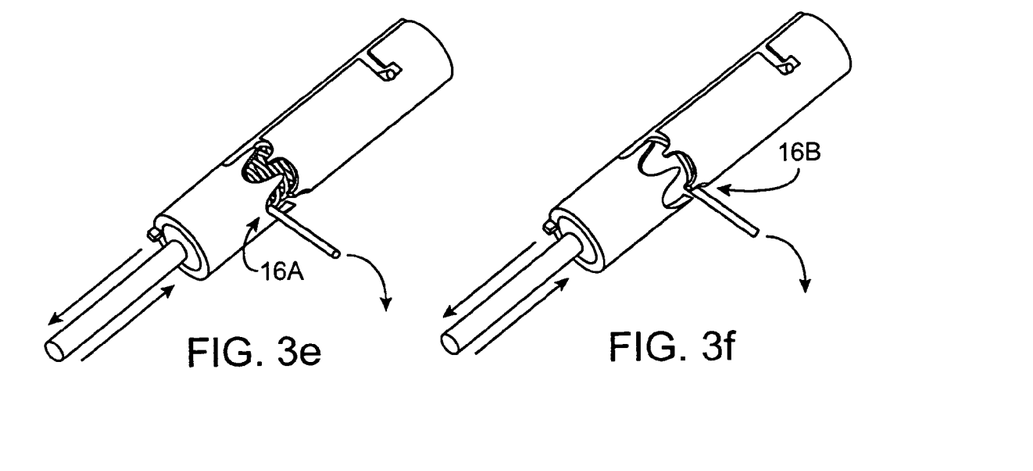
Figure 4:
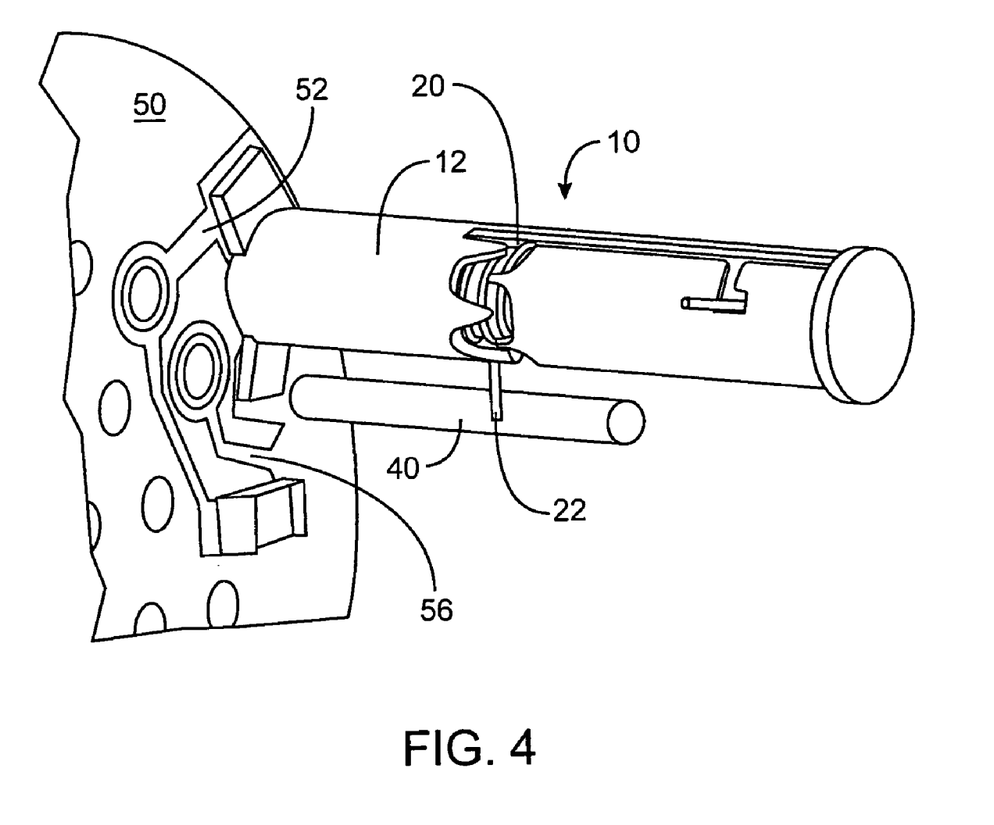
FIG. 4 is a perspective view of the switch shown in FIG. 2 mounted on a substrate to establish electrical continuity at a terminating position of the switch.

When fully assembled, the switch 10 is shown in a perspective view in FIG. 2. The operation of the switch 10 can be seen by reference to FIGS. 3a-3f. FIG. 3a shows the switch 10 in a first position at the start of operation in which the member 22 rests in the first trough 16b of the pattern 16. After plunger 30 is moved in an axial direction urging against the spring 20, the member 22 traverses along the pattern 16 in an axial direction and in a radial direction, due to the pre-tension of the spring 20. The result of the plunger 30 pressed to the fullest extent against the spring 20 is shown in FIG. 3b in which the member 22 rests against the crest 16a in the pattern 16. When force is released from the plunger 30 urging against the spring 20, the axial compression force of the spring 20 pushes the plunger 30 back. In addition, because the spring 20 is pre-stressed in the radial direction, the member 22 would then traverse the pattern 16 causing the spring 20 to rotate. This brings the member 22 of the spring 20 to rest against the next trough 16b in the pattern 16. The result is shown in FIG. 3c. This completes one operation of the switch 10. The number of operations that the switch 10 can operate is predetermined by the number of crests 16a and troughs 16b of the pattern 16. Thus, another operation of the switch 10 would causes the member to be pressed to another crest 16a in the pattern 16 (See FIG. 3d), followed by the member 22 coming to rest against another trough 16b (See FIG. 3e) in the pattern 16. This completes another use of the switch 10. Another use of the switch 10 causes the member 22 to move in the pattern 16 to another crest 16a (See FIG. 3f) followed by a return to another trough 16b in the pattern 16 (See FIG. 4), to the final position. At the final position, the member 22 may make electrical contact to establish electrical continuity with a contact pin 40, as shown in FIG. 4.

The switch 10 can be used in a medical or surgical device; the switch 10 is mounted on a substrate 50. Preferably, the substrate 50 is a printed circuit board connector of the type disclosed in U.S. patent application Ser. No. 10/171,698 filed on Jun. 17, 2002, assigned to the present assignee, whose disclosure is incorporated by reference in its entirety. As seen in FIG. 4, the switch 10 is mounted on the printed circuit board connector 50. In the embodiment shown in FIG. 4, the spring 20 is made of metal, the contact pin 40 is made of metal, and the housing 12 is also made of metal. The housing 12 can be mounted on the substrate 50 by press fit, surface mount, through-hole mounting, "mosquito" clip mounting, adhesive mounting, molded-in mounting, or snap-fit mounting into a preformed shape. The spring 20 and the housing 12 are electrically connected to the electrical tracing 52 on the printed circuit board connector 50. The contact pin 40 is also mounted on the printed circuit board connector 50 spaced apart from the switch 10. The contact pin 40 is also electrically connected to an electrical tracing 56 on the printed circuit board connector 50. The printed circuit board connector 50 can be used in a medical/surgical hand piece or electrical connector 70 to perform various medical/surgical procedures. The hand piece or receptacle electrical connector 70 is typically electrically connected to a medical/surgical connector 72 (shown in FIG. 8).

When the hand piece or receptacle electrical connector 70 is connected to the plug connector 72, the device can be used to perform the medical/surgical procedure. With the hand piece or receptacle electrical connector 70 is connected to the plug connector 72, the plug connector 72 urges the plunger 30 pushing it to cause the member 22 to come to rest at a crest position 16a in the pattern 16. After the procedure or one unplugging cycle, the hand piece or receptacle electrical connector 70 is removed from the plug connector 72. This causes the plunger 30 to return the member 22 to a trough position 16b in the pattern. The hand piece or receptacle electrical connector 70 is then sometimes subject to a sterilizing procedure. After the hand piece or receptacle electrical connector 70 is sterilized or just plugged in again, it is connected back to the plug connector 72, causing the plug connector 72 to urge the plunger 30 against the spring 20, and causing the member 22 to be pushed to another crest position 16a in the pattern 16. This action of connecting or reconnecting the hand piece or receptacle electrical connector 70 to the plug connector 72 causing the plug connector 72 to push the plunger 30 causing the member 22 to move to a crest position 16a in the pattern 16, and removing the hand piece 70 from the or receptacle electrical connector connector 72 causing the member to move to a trough position 16b repeats until the member 22 comes to contact against the contact pin 40 (as shown in FIG. 4). At that position, electrical contact is established between the electrical trace 52, the housing 12, the member 22 of the spring 20, to the contact pin 40 to the electrical tracing 56. When contact is so made, the switch 10 can cause electrical continuity to be established. This could cause the controller 72 not to provide any power to the hand piece or receptacle electrical connector 70. This would then cause the hand piece or receptacle electrical connector 70 to stop functioning. The number of operations that the hand piece or receptacle electrical connector 70 can be used is determined by the number of crests and troughs in the pattern 16, which are pre-set at the factory when the hand piece or receptacle electrical connector 70 is first assembled.

Figure 5A:
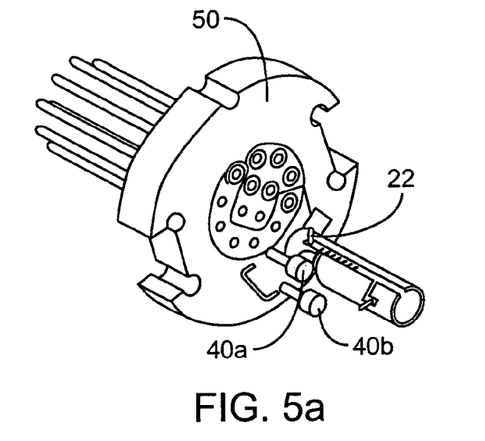
FIGS. 5a-5e are perspective views showing the operation of the switch shown in FIG. 2 mounted on a substrate wherein the switch at the terminating position breaks electrical continuity.
Figure 5B:
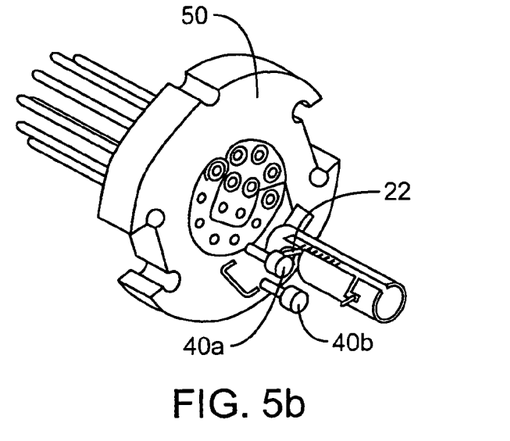
Figure 5C:
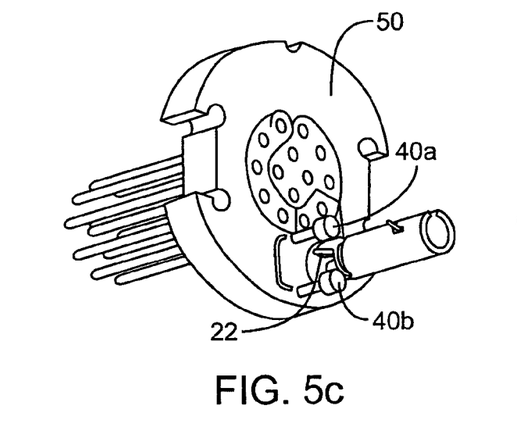
Figure 5D:
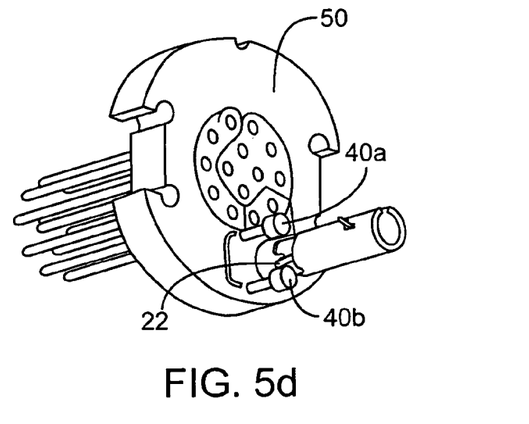
Figure 5E:
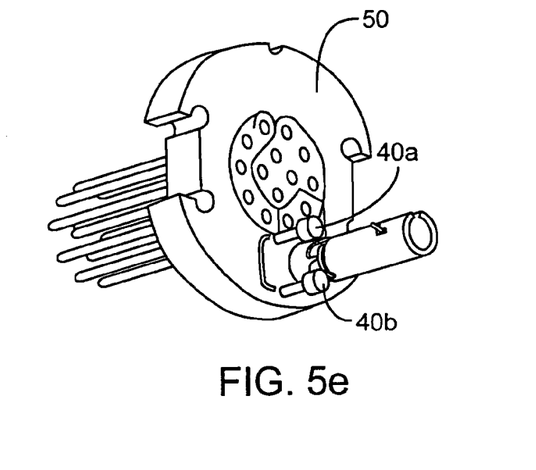

Referring to FIGS. 5a-5e there is shown a series of perspective views of a switch 10 mounted on a substrate 50 with the member 22 moving to contact a plurality of contact pins 40(a-b). Each of the contact pins 40 has a bulge like portion at its end. The bulge like portion is positioned near the crest portion 16a of the pattern 16. FIG. 5a shows the initial position of the switch 10 in which the member 22 is not in contact with either of the contact pins 40a or 40b. When the plunger 30 is urged against the spring 20, the member 22 is moved axially and radially to the position shown in FIG. 5b. At that location, the member 22 contacts the bulge like portion of the first contact pin 40a establishing electrical continuity with the contact pin 40a. When the hand piece 70 is disconnected from the plug connector 72, the member 22 traverses to a trough portion 16b of the pattern 16, as shown in FIG. 5c. At that location, the member 22 does not contact either of the contact pins 40a or 40b. When the hand piece 70 is connected to the plug connector 72 again, the plunger 30 is urged against the spring 20 causing the member 22 to move to the next crest position 16a of the pattern 16. At that location, the member 22 contacts the bulge like portion of the second contact pin 40b, thereby establishing electrical continuity. Finally, when the hand piece or receptacle electrical connector 70 is removed from the plug connector 72, the member 22 traverses to the terminating position, wherein the member 22 does not make electrical contact with either contact pins 40a or 40b. Thus, in this embodiment, through a change in the shape of the contact pin 40, and the location, and the pattern 16, the switch can be used to establish electrical continuity during the positions in which the plunger 30 is activated, and to break electrical continuity when the member reaches the terminating position.

Figure 6A:
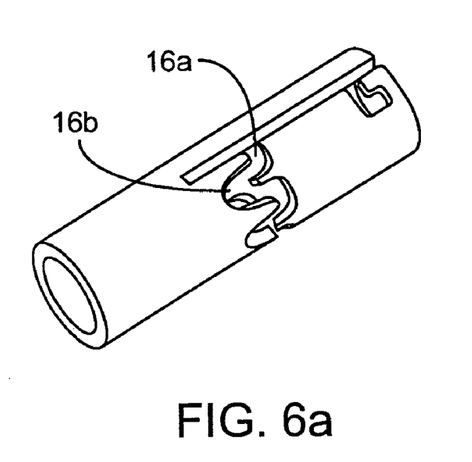
FIG. 6a is a perspective-enlarged view of the housing of the switch shown in FIG. 2, and the pattern through which the member traverses.
Figure 6B:
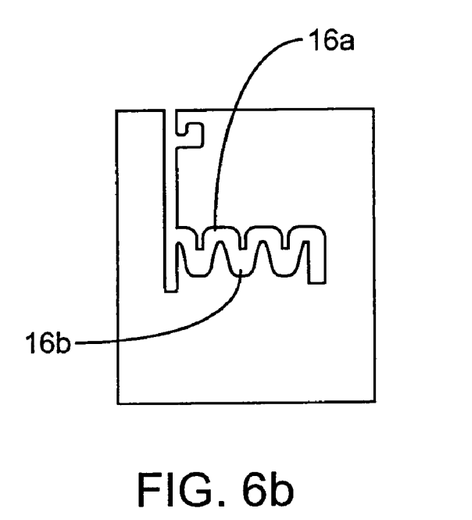

Referring to FIG. 6a there is shown an exploded view of the housing 12 with the pattern 16. The pattern 16 (as shown in FIG. 6b) as previously discussed has one or more crests 16a and one or more troughs 16b. The number of crests 16a and troughs 16b determines the number of activations of the switch 10 at the end of which either electrical continuity is established or electrical continuity is broken. The distance between each crest 16a and adjacent trough 16b is determinative of the distance of the throw of the plunger 30 by which the plunger 30 must move to activate each operation. This distance is further determinative of the amount of force required for the activation of the switch 10. The distance and depth of the pattern also make it possible to require that the connector be fully engaged to make electrical contact with the sensing resistor pins which can be shortened.

Figure 7:
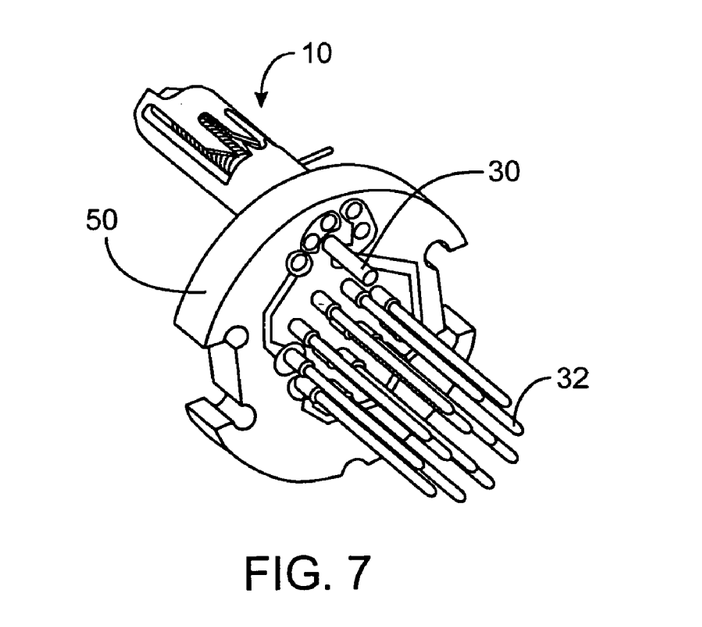
FIG. 7 is a perspective view of the switch shown in FIG. 2 mounted on a substrate, showing the plunger through the substrate and the relationship of the size of the plunger to the other signal connectors of the substrate.

Referring to FIG. 7 there is shown a perspective view of the underside of the substrate 50 on which the switch 10 is mounted to one side. As shown in FIG. 7, the substrate 50 has a plurality of electrical signal pin connectors 32 mounted on the underside. The plunger 30 passes through the opening in the substrate 50. The length of the plunger 30 can be chosen to be shorter than the other electrical signal pin connectors 32. This feature assures that the user must fully engage the hand piece or receptacle electrical connector 70 to the plug connector 72, and move the plunger 30 thereby activating the switch 10. This thwarts any attempt to defeat the limitation of the activation of the switch 10.

Figure 8:
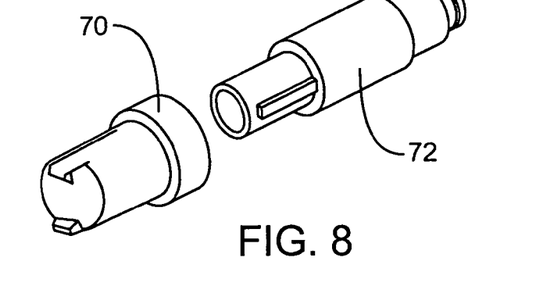
FIG. 8 is a perspective view of the mechanical limiter switch of the present invention, mounted on a substrate and assembled into a medical/surgical device which is mounted into a connector which can be mounted into a hand piece.

As previously discussed, the substrate 50 can be mounted in a hand piece or receptacle electrical connector 70, which is used in the medical/surgical procedure, and which after the procedure must be appropriately sterilized. The hand piece or receptacle electrical connector 70 is connected to a plug connector 72 as shown in FIG. 8. However, the switch 10 of the present invention can also be mounted in the plug connector 72 rather than in the hand piece or receptacle electrical connector 70. This is one application of the present invention.

Figure 9A:
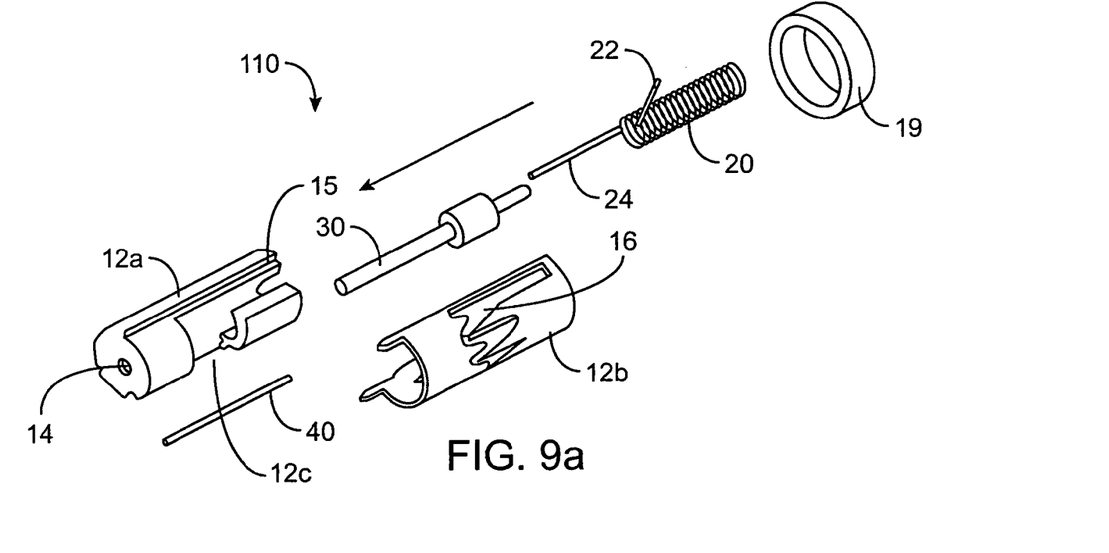
FIG. 9a is an exploded perspective view of another embodiment of the mechanical limiter switch of the present invention.
Figure 9B:
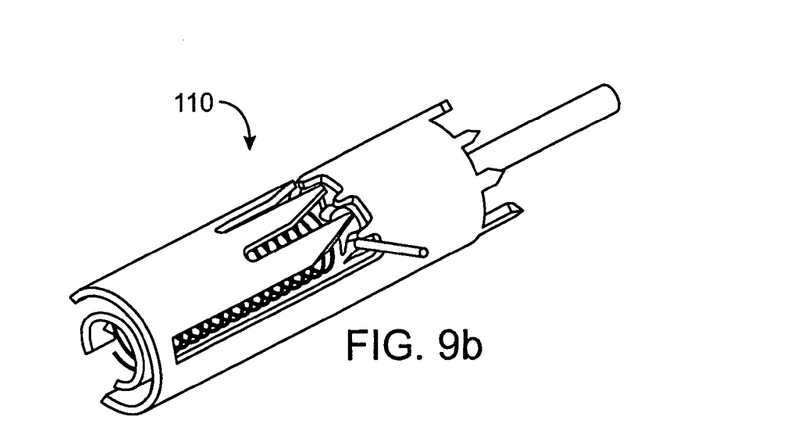

Referring to FIG. 9a, there is shown an exploded view of another embodiment of a switch 110 of the present invention. The switch 110 has many components similar to the components of the switch 10. The switch 110 comprises a housing 12 having two parts 12a and 12b. The first part 12a is made of plastic and is substantially cylindrically shaped. The housing 12a has a central axial opening 14, radial opening 12c, and a notch 15 along its axial direction. The second part 12b of the housing 12 is of metal and is a cover plate covering portions of the first part 12a, and having the pattern 16. A plunger 30 is mounted axially through the axial opening 14 of the housing 12. A spring 20 has a radially protruding member 22, near a first end. The second end 24 of the spring 20 is bent axially. The spring is mounted axially into the axial opening 14 of the housing 12, with the member 22 protruding through the pattern 16 of the second part 12b, and with the second end 24 in the axial notch of the first part 12a. A cap 19 encloses one end of the housing 12. A fully assembled switch 110 is shown in FIG. 9b. Functionally, the switch 110 works just like the switch 10. However, unlike the embodiment shown in FIG. 1, the switch 110 does not require an external contact pin 40 for operation. A contact pin 40 can be mounted within the housing 12 if it is desired to established electrical continuity when the member 22 contacts the pin 40. Alternatively, the contact pin 40 can be removed and the switch 110 operates so that electrical continuity is always established until the member 22 reaches a terminating position, at which point the electrical continuity is broken. The two methods of operation are explained as follows.

If it is desired to establish electrical continuity at the end of the traversal of the member 22, contact pin 40 is placed in the housing 12. The contact pin 40 is insulated from the conductive portion 12b of the housing 12. Electrical contact on the substrate 50 is established to the spring 20 and to the contact pin 40. In this manner, as the member 22 traverses the pattern 16, it establishes electrical continuity when the member 22 contacts the contact pin 40.

If it is desired to break electrical continuity at the end of the traversal of the member 22, contact pin 40 is removed from the housing 12. Electrical contact on the substrate 50 is established to the plunger and to the metal portion 12b of the housing 12. In this manner, as the member 22 traverses the pattern 16, it continually establishes electrical continuity with the metal portion 12b of the housing 12. When the member reaches its terminating position, it would contact the insulating portion 12a of the housing 12, thereby breaking electrical continuity.

Figure 10A:
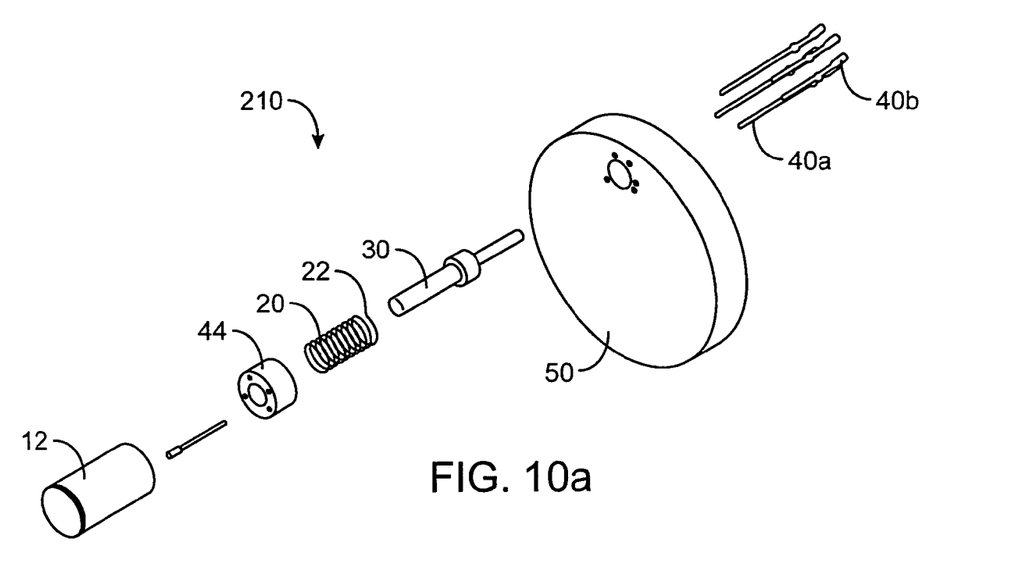
FIG. 10a is an exploded perspective view of yet another embodiment of the mechanical limiter switch of the present invention.
Figure 10B:
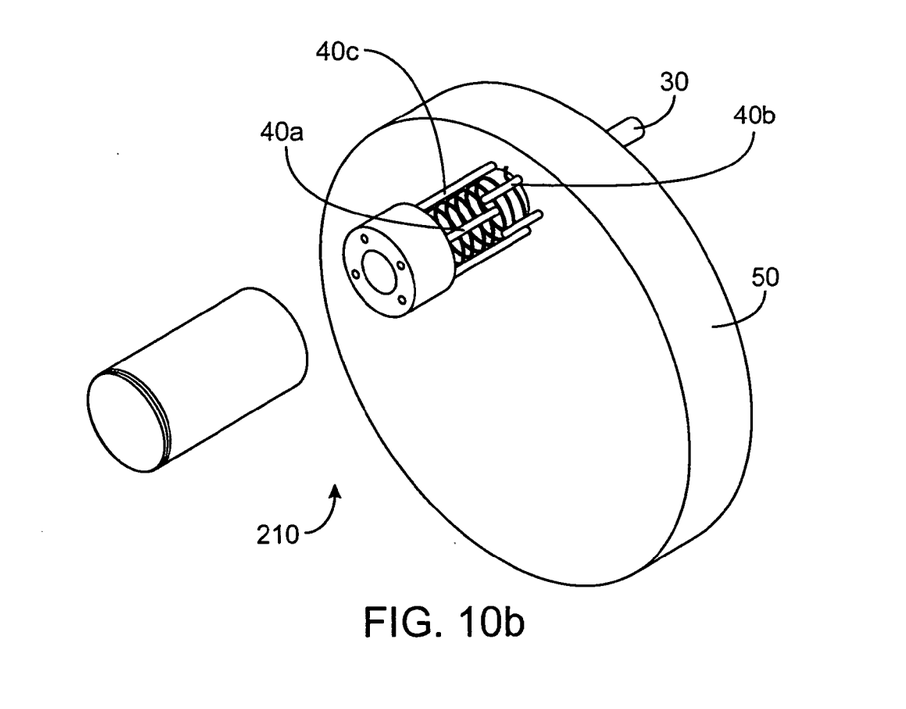

Referring to FIG. 10a there is shown an exploded perspective view of yet another embodiment of a switch 210 of the present invention. The switch 210 has many components similar to the components of the switch 10, and 110. The switch 210 is mounted on a substrate 50, which has an axial opening there through. A plunger 30 is mounted in the axial opening and urges a spring 20 against an end cap 44. The spring 20 has a radially protruding member 22, near a first end. The second end 24 of the spring 20 abuts the end cap 44. The spring 20 is mounted axially into the axial opening of the substrate 50. A plurality of posts 40a and 40b are positioned around the opening in the substrate and around the plunger 30. Some of the posts 40b are mounted on the substrate 50 and extend outward to the end cap 44. Some of the posts 40a are mounted on the end cap 44, and extend downward to the substrate 50. Thus, there exists a gap between the posts 40a and the posts 40b. One of the posts 40c extends from the substrate 50 to the end cap 44. The member 22 is positioned to protrude through the gap between the posts 40a and 40b and traverses the pattern formed by the gap until it reaches the end of its traversal and contacts the post 40c, which extends between the substrate 50 and the end cap 44. A housing 12 may enclose the end cap 44, the spring 20 and the posts 40a, and 40b. A fully assembled switch 210 is shown in FIG. 10b. Functionally, the switch 210 works just like the switch 10 or 110. However, unlike the embodiment shown in FIG. 1 or 9, the housing 12 does not have a pattern through which the member 22 protrudes and through which the member 22 traverses. Rather, the pattern is formed by the gaps between adjacent posts 40a and 40b, mounted on the substrate 50 and on the end cap 44 respectively. Further, because of the end cap 44, other electrical components, such as resistors and capacitors can be mounted on the end cap 44, and electrically connected to the various posts 40a, 40b or 40c, attached to the end cap 44. Similar to the operations described for the switch 10 or the switch 110, the switch 210 has two modes of operation. In a first mode, as the member 22 traverses the gap between adjacent posts 40a and 40b, it establishes electrical continuity, and at the end of its traversal when it contacts post 40c, electrical continuity is broken. The second mode of operation is where the member 22 traverses the gap between the adjacent posts 40a and 40b and establishes electrical continuity at the end of its traversal when it contacts post 40c. The two methods of operation are explained as follows If it is desired to establish electrical continuity at the end of the traversal of the member 22, the post 40c is made of a metal, and all the other posts 40a and 40b are made of an insulating material. Electrical contact on the substrate 50 is established to the plunger 30, which contacts the metal spring 30, and to the terminating post 40c. In this manner, as the member 22 traverses the gap between the posts 40a and 40b, it establishes electrical continuity only when the member 22 contacts the terminating posts 40c.

If it is desired to break electrical continuity at the end of the traversal of the member 22, the post 40c is made of an insulator, and all the other posts 40a and 40b are made of metal. Electrical contact on the substrate 50 is established to the plunger 30, which contacts the metal spring 30 and to all the other posts 40a and 40b. In this manner, as the member 22 traverses the gap between the posts 40a and 40b, it establishes electrical continuity with each of the posts 40a or 40b, and when the member 22 contacts the terminating posts 40c, it breaks electrical continuity.

Figure 11A:
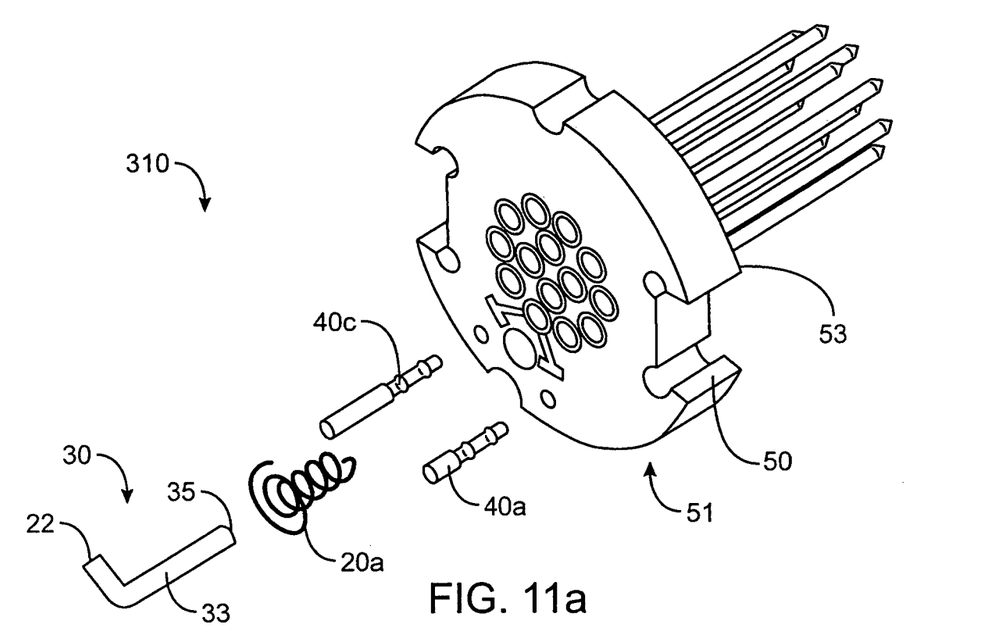
FIG. 11a is an exploded perspective view of still yet another embodiment of the mechanical limiter switch of the present invention.
Figure 11B:
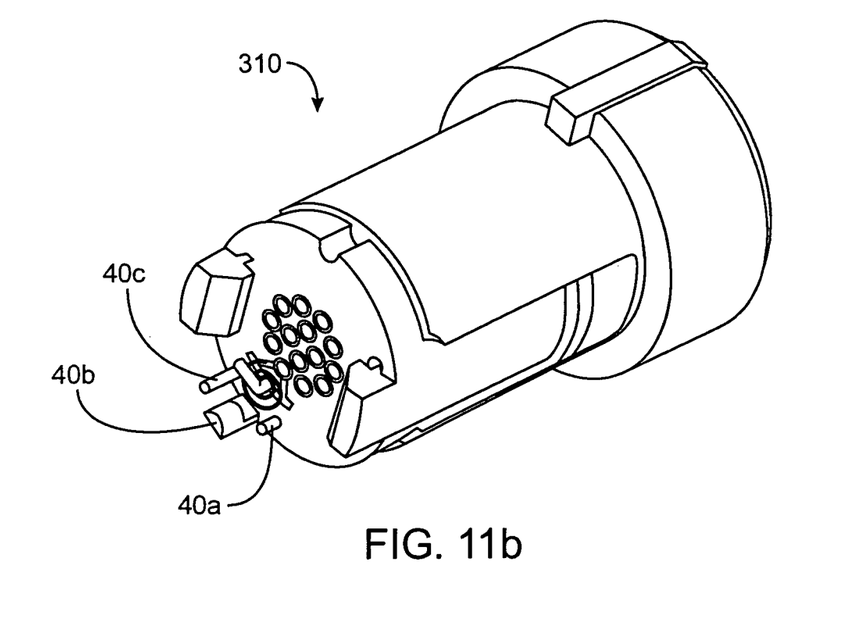

Referring to FIG. 11a there is shown an exploded perspective view of still yet another embodiment of a switch 310 of the present invention. The switch 310 has many components similar to the components of the switch 10, 110 and 210. The switch 310 is mounted on a first surface 51 of the substrate 50, which has an axial opening there through. A plunger 30 is mounted in the axial opening. The plunger 30 has two parts, a member portion 22, which extends substantially in a radial direction, and an axial portion 33. The axial portion has an end 35. The plunger 30 urges a first spring 20 against the first surface 51. The axial portion 33 of the plunger is positioned through the axial opening in the substrate 50. A retaining clip (not shown) is attached to the end 35 of the axial portion 33, thereby preventing the plunger 30 from coming out of opening in the substrate 50. A second spring (not shown) is positioned between the second surface 53 (the surface opposite the first surface 51) of the substrate 50 and the retaining clip. The second spring is stronger than the first spring 20a. Thus, when assembled the plunger 30 urges against the first spring 20a to the first surface 51 of the substrate 50. The first spring 20a is pre-tensioned to rotate in a radial direction. A plurality of posts 40a, 40b and 40c are mounted on the first surface 51 of the substrate 50 around the opening through which the plunger 30 is positioned. Each of the posts 40a, 40b and 40c can be of different sizes and of different material to accommodate the two modes of operation for the switch 310. A fully assembled switch 310 is shown in FIG. 11b. Unlike the switches 10, 110 or 210, there is no housing 12 whatsoever, nor any pattern through which the member 22 traverses. Similar to the switch 10, 110 and 210, the switch 310 can be operated in one of two modes. In a first mode, as the member 22 rotates and impinges the different posts 40a, 40b and 40c it establishes electrical continuity, and at the end of its traversal it breaks electrical continuity. The second mode of operation is where the member 22 rotates and establishes electrical continuity at the end of its rotation. The two methods of operation are explained as follows If it is desired to establish electrical continuity at the end of the rotation of the member 22, the post 40c is made of a metal, and all the other posts 40a and 40b are made of an insulating material. The post 40a is of low height such that after a use, and the hand piece or receptacle electrical connector 70 is withdrawn; the member 22 comes to rests against the first post 40a. When the hand piece 70 is again connected to the plug connector 72, the plunger is axially moved, causing the member to be at a height above the post 40a, thereby causing it to rotate to the member 40b. This continues until the member 22 comes to rest at the post 40c. The post 40c is of sufficient height such that further axial movement of the plunger 30 would not cause the member 22 to pass over the top portion of the post 40c. Electrical contact on the substrate 50 is established to the plunger 30 and to the terminating post 40c. In this manner, as the member 22 rotates, it establishes electrical continuity only when the member 22 contacts the terminating posts 40c.

If it is desired to break electrical continuity at the end of the rotation of the member 22, the post 40c is made of an insulator, and all the other posts 40a and 40b are made of metal. Electrical contact on the substrate 50 is established to the plunger 30 which contacts all the other posts 40a and 40b. In this manner, as the member 22 rotates, it establishes electrical continuity with each of the posts 40a or 40b, and when the member 22 contacts the terminating posts 40c, it breaks electrical continuity.

There are many advantages to the switch of the present invention. First, it relies entirely upon mechanical action to establish electrical continuity or to break established electrical continuity. Thus, it can withstand the rigor of x-ray or other harsh sterilization environment. It can be factory pre-set to limit the number of uses. It does not require changes to existing equipment, i.e. controller of the medical device to which it is attached. Indeed, if an external controller is used, it does not require changes to the external controller. It is small enough to fit within an existing device. Finally, the switch is inexpensive.

What is claimed is:

1. A limiter switch assembly comprising:
   means for enclosing the assembly;
   means for establishing and disconnecting electrical connectivity associated with the assembly; and
   means for manually controlling the establishment and disconnection of electrical connectivity.

2. The assembly of claim 1, wherein the means for enclosing comprises a housing, the means for establishing and disconnecting electrical connectivity comprises a spring positioned inside the housing and a passageway defined through a wall of the housing, with the spring being coupled to the passageway via a protrusion that either establishes or disconnects the electrical connectivity of the assembly depending upon the location of the protrusion in the passageway, and the means for controlling is a plunger coupled to the spring and the housing, said plunger being movable within the housing.

3. The assembly of claim 2, wherein the spring is coupled to the protrusion that extends into the passageway and the passageway has a shape that provides a single path of travel for the protrusion, wherein the protrusion together with the housing establishes electrical connectivity at at least one predetermined travel location of the protrusion within the passageway.

4. The assembly of claim 3, wherein the passageway is shaped like a plurality of teeth such that the protrusion travels up and down around the teeth in response to movement of the plunger.

5. A limiter switch assembly comprising:
a movable member utilized for establishing and disconnecting electrical connectivity;
means for retaining the movable member;
a manually operated plunger for moving the movable member; and
at least one electrically conductive material for mating with the movable member such that when the movable member is associated with the electrically conductive material, the assembly is one of activated or deactivated;
wherein the movable member is configured to provide one or more activations of the assembly.

6. The assembly of claim 5, further comprising at least one insulating material for associating with the movable member, wherein the movable member is configured for both radial and axial movement out of and into electrical connectivity with the electrically conductive and insulating materials, respectively, with the activation of the assembly occurring when the movable member is associated with one of the electrically conductive material or the insulating material.

7. A mechanical switch system comprising:
a housing having a plurality of impediments for establishing and disconnecting an electrical connectivity of the switch; and
a contact member movably associated with the impediments,
wherein the position of the contact member relative to the impediments determines whether or not electrical connectivity is established, and the impediments are configured to restrict and guide movement of the contact member as it travels at least one of axially and radially relative to the impediments.

8. The system of claim 7, further comprising a spring mounted in the housing, with the contact member coupled to the spring; a plunger mounted in the housing and coupled to the spring to urge the spring's movement; and a circuit bearing structure, wherein the housing and plunger are coupled to the circuit bearing structure.

9. The system of claim 8, further comprising carrier pins for coupling the circuit bearing structure to the housing.

10. The system of claim 9, wherein the housing and circuit bearing structure are inseparably mounted together via the carrier pins.

11. The mechanical switch system of claim 7, wherein the plurality of impediments include at least one of conductive areas and nonconductive areas for interacting with the contact member.

12. The mechanical switch system of claim 7, wherein one or more of the plurality of impediments is configured to allow the contact member to move incrementally radially around one or more of the plurality of impediments when the contact member moves axially.

13. The mechanical switch system of claim 7, wherein the housing and contact member are configured to open or close an electrical circuit upon each axial and corresponding radial movement of the contact member across one of the impediments.

14. The mechanical switch system of claim 7, wherein the housing and contact member are configured to open or close an electrical circuit when the contact member moves around a final one of the plurality of impediments.

15. The mechanical switch system of claim 7, further comprising an electrical circuit coupled to one of the plurality of impediments.

16. The mechanical switch system of claim 7, wherein the housing comprises:
a first housing defined about an axis having a first perimeter surface encircling the axis and enclosing an opening on an axial end, said first housing also enclosing a first patterned opening in said perimeter surface;
a second housing defined about an axis having a second perimeter surface encircling the axis and extending to a greater radius than the first perimeter surface, said second housing enclosing a second patterned opening in said second perimeter surface;
said second housing enclosing said first housing; and
said first patterned opening having a portion in common with said second patterned opening to define the plurality of impediments.

17. The mechanical limiter switch of claim 16, wherein after a pre-determined number of axial movements of the plunger and corresponding movement of the movable member relative to the patterned opening, electrical connectivity of the switch is discontinued so that the switch is no longer operable to establish electrical connectivity.

18. The mechanical limiter switch of claim 16, wherein said first housing is made of an insulator and said second housing is made of a conductive material, and wherein said member is limited in its axial direction of traversal by the first patterned opening and is limited in the radial direction of traversal by the second patterned opening; and said member contacts said second patterned opening, whereby electrical connectivity is established.

19. The mechanical limiter switch of claim 16, wherein the first and second patterned openings comprise a zigzag pattern having one or more crests and one or more troughs.

20. A mechanical limiter switch of claim 7, further comprising at least one of a medical or surgical device having an electrical connection, wherein the mechanical limiter switch is coupled to the electrical connection of the device for limiting activation of the device.

* * * * *